(12) United States Patent
Parks

(10) Patent No.: US 6,710,083 B2
(45) Date of Patent: Mar. 23, 2004

(54) METHOD OF TREATING PALMAR AND PLANTAR FIBROMATOSIS

(76) Inventor: L. Dean Parks, 2420 SE. 15th St., Ocala, FL (US) 34471

( * ) Notice: Subject to any disclaimer, the term of this patent is extended or adjusted under 35 U.S.C. 154(b) by 0 days.

(21) Appl. No.: 10/191,253

(22) Filed: Jul. 9, 2002

(65) Prior Publication Data

US 2004/0010041 A1 Jan. 15, 2004

(51) Int. Cl.⁷ .................. A61K 31/07; A61K 31/045; A61K 31/00; A61J 3/10; A61B 17/22
(52) U.S. Cl. .................. 514/559; 514/725; 514/801; 514/802; 514/859; 514/863; 514/885; 514/962; 424/464; 424/489
(58) Field of Search ................... 514/725, 559, 514/801, 802, 859, 863, 885, 962; 424/464, 489, 278.1

(56) References Cited

PUBLICATIONS

The Merck Manual, Sec. 5, Ch. 61, Common Hand Disorders, p. 1.*
Ellis et al., Uses and Complications of Istreotonin Therapy, Journal of the American Academy of Dermatology, vol. 45, No. 5, 2001., See: pp. 1–16.*

* cited by examiner

*Primary Examiner*—Frederick Krass
*Assistant Examiner*—Clinton Ostrup
(74) *Attorney, Agent, or Firm*—Melvin K. Silverman; Yi Li

(57) ABSTRACT

A method of treating palmar and plantar fibromatosis is disclosed. The method includes administering to a patient of a therapeutically effective amount of a composition comprising 13-cis-retinoic acid. Preferably, the treatment method includes administering to a patient of an initial dosage of a composition comprising 13-cis-retinoic acid for an initial treatment period, and thereafter administering a maintenance dosage of the composition.

12 Claims, No Drawings

METHOD OF TREATING PALMAR AND PLANTAR FIBROMATOSIS

FIELD OF THE INVENTION

The present invention relates to a method for treatment of palmar and plantar fibromatosis. More specifically, the method utilizes 13 cis-retinoic acid to effectively treat palmar and plantar fibromatosis.

BACKGROUND OF THE INVENTION

Palmar fibromatosis, also called Dupuytren's contracture, Dupuytren's disease, palmar fasciitis, and Viking disease, is a thickening and tightening of the fibrous tissue beneath the skin on the palm of the hand, causing bending of fingers. Plantar fibromatosis is the same problem occurring on the soles of the feet.

In the palms of our hands and the soles of our feet, there are strips of fibrous tissue called fascia (the palmar fascia and plantar fascia, respectively), which are usually soft and pliable. For people having palmar fibromatosis, this tissue becomes thickened and contracted, causing tight cords or nodules under the skin and resulting progressive bending of the fingers. The process starts usually at the crease on the palm of the hand, and progresses to involve the joint at the base of the finger, then the next joint of the same finger. A small, painless nodule develops in the connective tissue and eventually develops into a cord-like band. Extension of the fingers becomes difficult to impossible with advanced cases. The fingers are relentlessly drawn inward into a rigid fist. As flexibility goes away, so does the useful functions of the hand. It has been found clinically that the ring finger is affected most-often followed by the little, middle, and index fingers. The condition can appear suddenly, but usually it is a slow, progressive process.

Dupuytren's contracture is common. It occurs most commonly in men over 45 years of age. The incidence is higher among people who are alcoholics, and people with diabetes, epilepsy, and pulmonary disease such as emphysema or chronic bronchitis.

In plantar fibromatosis, this same relentless contracture happens in the soles of the feet, drawing the toes downward, folding the feet into a frozen fist, and making it impossible to walk. Plantar fibromatosis is much less common, but patients suffer a severe pain because structural distortions of the feet affects walking. Presently, most plantar fibromatosis patients are constrained to the wheelchairs because of the structural distortion of their feet.

The cause of palmar and plantar fibromatosis is unknown, but genetic predisposition appears to play a role. It is commonly seen that the diseases pass on in a family from generation to generation. Palmar fibromatosis was first described by Baron Guillaume Dupuytren, French surgeon of the early 1800's who was successful with the surgical treatment of this condition, and hence named after him as Dupuytren's contracture. By carefully cutting the involved fascia, Dupuytren was able to achieve good results, for a period of time. However what had caused the fascia to grow abnormally before, caused the regrowing fascia to eventually contracture and thicken again. Therefore, for over 100 years the condition was thought to be relentlessly progressive.

Current treatment involves observation at first when the process is in the early stages. Exercises, warm water baths, or splints may be helpful. Injection of a corticosteroid medication into the nodule may help the tenderness and delay the progression of the diseases. Currently, surgery is essentially the only treatment for the disease, because surgery divides the cords and removes scar tissue, which allows the fingers to straighten. Surgery is usually recommended when the contracture is significant, for example, for patient of palmar fibromatosis when the hand cannot be placed flat on a table. However, reoccurrence of the diseases after surgery is frequent. It is also believed that surgery accelerates the reoccurrence, and worsening of the condition. Additionally, the small nerves and blood vessels to the fingers are at risk of injury during surgery. Other problems with surgery include bleeding under the skin. As well as infection is possible after any surgical operation.

Because of the lack of effective treatment for palmar and plantar fibromatosis, and the disabling nature of the disease, there are active research projects seeking for solutions for treating the disease. In one recent approach, physicians can differentiate between normal fascia and abnormal fascia which maybe normal-appearing by means of electron microscopy and DNA analysis. By carefully removing all of the involved plantar fascia with a wide margin of normal fascia, surgeons at Brown University have achieved excellent results in treating plantar fibromatosis (Plastic and Reconstructive Surgery, Feb. 1989). However, this surgery is technically very difficult.

Another recent development in the treatment of Dupuytren's contracture is the continuous elongation technique, pioneered by Doctors Messina and Messina of Turi, Italy, which appears to enhance both short- and long-term results (Plastic and Reconstructive Surgery, July 1993). With this method, a device is affixed to a bone in the hand or foot to provide a steady, painless stretching of the contracting fascia. This preparatory step is used in severe Dupuytren's contracture before excision of the affected fascia (Journal of Hand Surgery, June 1996). The nonsurgical treatments, radiotherapy and injections of superoxide dismutase, have now been shown not to work.

Currently, no systemic medication is known that can treat palmar and plantar fibromatosis.

13-cis retinoic acid, more generally known as retinoic acid, also referred to as isotretinoin, and sold under the trademark Accutane® from Hoffmann-La Roche Inc., Nutley, New Jersey, has long been known as a topical and oral dermatological agent used in the treatment of acne vulgaris and several other skin diseases. 13-cis retinoic acid inhibits sebaceous gland function and keratinization. The exact mechanism of action of Accutane in treating acne is unknown. Since retinoic acid is a teratogenic drug and, because of the mutagenic effects associated with such drugs, it is only used for treating severe acne vulgaris when other treatments are not effective.

Since 1992 there have been literature reports on the potential effect of 13-cis-retinoic acid upon human prostate cancer cells. U.S. Pat. No. 5,612,354 (to Sanz et al) discloses a method of treating mammals suffering from disorders which are characterized by an increased proliferation or abnormal differentiation of cells by the systemic or topical administration to the mammals of an effective amount of (1H-azol-1-ylmethyl) substituted quinoline derivatives, including 13-cis-retinoic acid. It is believed that because of the capability to delay the metabolism of retinoic acid, (1H-azol-1-ylmethyl) substituted quinoline derivatives may potentially be used in treating cancers.

As described above, it is apparent that there is a strong need for medications that can effectively treat palmar and plantar fibromatosis. Because of complete lack of non-surgical treatments, and frequently recurrence of the diseases after surgeries, a medication that can cure the disease or inhibit further progress of the contracture will have important clinical significance for millions of people who suffer from palmar and plantar fibromatosis.

SUMMARY OF THE INVENTION

In one embodiment, the present invention relates to a method of treating palmar and plantar fibromatosis, which comprises administering to a patient of a therapeutically effective amount of a composition comprising 13-cis-retinoic acid. The composition further comprises a pharmaceutical carrier, and the composition can be in the forms of powder, pill, capsule, tablet, and liquid. Preferably, the method of treating palmar and plantar fibromatosis comprises the steps of: administering to a patient of an initial dosage of a composition comprising 13-cis-retinoic acid for an initial treatment period; and thereafter administering a maintenance dosage of the 13-cis-retinoic acid composition.

In a further embodiment, the present invention relates to a method of treating palmar and plantar fibromatosis, which combines a surgical procedure and administration of a therapeutically effective amount of composition comprising 13-cis-retinoic acid.

It is accordingly an object of the present invention to provide a medicine for treating palmar and plantar fibromatosis and related symptoms.

It is further object to provide a non-surgical method for treating palmar and plantar fibromatosis.

The above and yet other objects and advantages of the present invention will become apparent from the hereinafter set forth Detailed Description of the Invention and claims appended herewith.

DETAILED DESCRIPTION OF THE INVENTION

In one embodiment, the method of the present invention is directed to a method of treating palmar and plantar fibromatosis. The method comprises administering to a patient of a therapeutically effective amount of a composition comprising 13-cis-retinoic acid. The therapeutically effective amount is in a range from about 10 mg to about 80 mg of 13-cis-retinoic acid of an average daily intake (about 0.14 mg to about 1.1 mg per kilogram (kg) of body weight).

The composition further comprises a pharmaceutical carrier. Common pharmaceutical carriers include liquid carriers such as water, glycols, oils, alcohols, syrups, and the like in the case of oral liquid preparations such as suspensions, syrups, elixirs and solution; and solid carriers such as starches, sugars, kaolin, lubricants, binders, disintegrating agents and the like in the case of powders, pills, capsules, and tablets; and other pharmaceutical carriers known in the art. The composition used for the purpose of the present invention can be in various forms, such as powders, pills, capsules, tablets, and liquids. Although oral administration is preferred because of its convenience, other suitable systemic administrations can also be used for the purpose of the present invention.

13-cis-retinoic acid is commercially available as a medicine under the trade name Accutane® from Hoffmann-La Roche Inc., Nutley, N.J. for treating certain dermatological diseases. Accutane® has three available doses, 10 mg, 20 mg, and 40 mg soft gelatin capsules.

Preferably, the treatment method further includes two treatment periods: an initial treatment, and a maintenance treatment. First, in the initial treatment a patient administrates an initial dosage of 13-cis-retinoic acid for a period from about ten days to about five months. Thereafter, the patient administrates a lower maintenance dosage of 13-cis-retinoic acid.

Preferably, the initial treatment period is about two to three weeks, because beyond two to three weeks side effects of the medicine, such as tenderness at sites of old injuries to the fibro-musculo-skeletal system, dry skin, chapped lips, dry eyes, and dry nose, tend to occur. If these side effects occur during the initial treatment period, they normally subside after the maintenance dosage is instituted. However, if a patient does not have adverse side effects, the initial treatment period can be extended accordingly to enhance the effect of the medication on the fibromatosis. Based on the fact that currently 13-cis-retinoic acid is used to treat severe acne patients for a continuous period of 20 weeks, the initial treatment period of the present invention can be substantially longer than several weeks depending on the responses and conditions of individual patients.

The low maintenance dosage has two functions. First, the treatment with the maintenance dosage, after the initial treatment, needs about eight to twelve months to eliminate or reduce already formed contracture, and to inhibit further progress of existing contracture for the patient who has severe conditions. Secondly, a long term administration of the maintenance dosage can prevent reoccurrence of contracture when it diminished with the treatment, and inhibit further progress of existing contracture. Therefore, preferably, the maintenance dosage is administered for long term.

The dosage is determined based on the patient's body weight. The initial dosage is in a range from about 10 mg to 80 mg 13-cis-retinoic acid daily (about 0.14 mg to about 1.1 mg per kilogram (kg) of body weight). For average men having a body weight about 160 lbs (72.6 kg), the average initial dosage is about 40 mg daily. The maintenance dosage is in a range from about 10 mg to 80 mg 13-cis-retinoic acid every three to seven days (about 0.14 mg to about 1.1 mg per kilogram (kg) of body weight). The average maintenance dosage for average men having a body weight about 160 lbs is about 40 mg every three to seven days. It is known that some children have been diagnosed with palmar and/or plantar fibromatosis. The dosages should be adjusted accordingly for children or those who weigh substantially less than or above the average body weight.

The daily dosage can be administrated in a single dose, or divided doses. Since Accutane® has three commercially available doses, 10 mg, 20 mg, and 40 mg soft gelatin capsules, for a 40 mg initially dosage, the patient can either take a 40 mg capsule, or take two 20 mg capsules daily, or take four 10 mg capsule daily. The same applies to the dosage in the maintenance treatment. For convenience, during the maintenance treatment the patients can take one 40 mg dose about every three to seven days.

It has been found that with the treatment using the method of the present invention the patients who were diagnosed with Dupytren's contracture achieved various degrees of improvements of their disease conditions. The observed improvements include reduction of fibrotic band in size and scope, softening or complete disappearance of fibrotic band of the affected fingers; reduction or disappearance of dimple overhead; recovery or improvement of the flexibility of the affected fingers; and reduction of pain and tenderness caused by the contracture. Furthermore, no serious adverse side effects were observed by using the described treatment.

Importantly, it has been found that the method of the present invention inhibits further progression of the contracture for patients who has either early stage of the disease, or advanced conditions. Therefore, the method of the present invention has an important clinical value in treating early stage of Dupytren's contracture to prevent progression of the disease into a disabling condition. In view of the disabling nature of this disease, and lack of prevention and non-surgical treatment, the discovery of the present invention is a significant breakthrough in terms of advancement of clinical treatment of palmar and plantar fibromatosis.

In a further embodiment, the method of the present invention can be used as an adjuvant to surgical procedures. A surgical procedure, conventional or newly developed procedure, can be utilized to remove the affected fascia, and administration of an effective amount of 13-cis-retinoic acid can be used to prevent or reduce reoccurrence of the disease. 13-cis-retinoic acid can be administered immediately after the surgery, and it can also be administered prior to the surgery to hinder the progression of the contracture.

Example 1 to 3 illustrate clinical effectiveness of the above described treatment method. An initial treatment and a maintenance treatment as described above were prescribed to the patients. It is noted that the patients described in the Examples were in the average weight range, therefore, an average dosage of 40 mg was used.

EXAMPLE 1

A white male patient was diagnosed of palmar fibromatosis on both hands. The patient's left hand middle finger was about 15 degree displaced in the flexed position, and his right hand middle finger was about 7 degree displaced in the flexed position, respectively.

The patient was treated with orally administering Accutane® (Hoffmann-La Roche Inc., Nutley, New Jersey) about 40 mg daily for 14 days. Then the dosage was decreased to a maintenance dosage of 40 mg about twice a week for twelve months.

After twelve month of therapy, the fibrotic band and dimpling overlying the flexor tendon of the middle fingers, bilaterally, softened and diminished in size and scope. On the left hand, the fibrotic band-completely disappeared, and on the right hand, it reduced from 4 mm to 2 mm. The dimple overhead of the third methocarpal bone disappeared on both hands.

Physical examination confirmed that range of "fixed" flexon of the left middle finger changed from 7 degree of flexon to none, leaving a full, normal range of motion, both for flexion and extension. The right middle finger improved from a fixed 15 degree of flexion as compared to the adjacent digits prior to the treatment to only 3 degree of fixed flexion. Furthermore, the patient described that pain and tenderness in the flexor tendon area of his hands completely abated.

No adverse side effects were noted other than drying of lips. Blood chemistries remained normal with the low maintenance dosage.

EXAMPLE 2

A 63 year old white male patient presented with history of long standing Dupytren's contracture of the left palm, with advanced disease conditions. The patient previously had a plastic repair and a "Z" plasty (a plastic surgery technique used for reducing scars and soft tissue contracture), but both treatments failed to improve or control his condition. His ring finger was about 90 degree displaced in the flexed position.

The patient was treated with orally administering Accutane® about 40 mg daily for 14 days. Then the dosage was decreased to 40 mg about twice a week for eight months.

During the eight month of therapy, the patient's conditions slowly improved. Physical examination found that the fibrotic ridge of the patient's left hand reduced in scope and size. The patient's ring finger's disposition from the flexed position reduced from about 90 degree to about 70 degree. The patient felt less tender of his left hand caused by the contracture.

The medication was well tolerated with the lower maintenance dosage. The patient had some musculoskelatal pain, which diminished after the third month of the treatment. No laboratory abnormality was observed.

EXAMPLE 3

A 61 year old white male patient presented with recently developed fibroplasia of his right hand. The condition had caused a 30 degree deflection of the right hand ring finger. The overlying skin was hypertrophic and hyperkeratotic from rubbing of his golf club. The Dupuytren's contracture band was thick and rigid, but without pain.

The patient was placed on Accutane® 40 mg daily for two weeks. Thereafter, the patient had a maintenance dosage of 40 mg about twice a week for nine months.

During the nine month of treatment, the patient achieved slow and steady improvement. The thickness of the fibrotic band reduced, and the restriction of extension of the ring finger lessened. Physical examination showed that the 30 degree deflection of the right hand ring finger prior to the treatment reduced to 20 degree. The patient described less tenderness in the flexor tendon area.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

What is claimed is:

1. A method of treating palmar and plantar fibromatosis comprising administering to a patient suffering from palmar or plantar fibromatosis a therapeutically effective amount of a composition comprising 13-cis-retinoic acid.

2. The method of claim 1, wherein said composition further comprises a pharmaceutical carrier.

3. The method of claim 2, wherein said composition is in a form selected from the group consisting of powder, pill, capsule, tablet, and liquid.

4. A method of treating palmar and plantar fibromatosis comprising the steps of:
   (a) administering to a patient suffering from palmar or plantar fibromatosis an initial dosage of a composition comprising 13-cis-retinoic acid for an initial treatment period, and
   (b) thereafter administering a maintenance dosage of said composition.

5. The method of claim 4, wherein said initial dosage is in a range from about 0.14 mg to about 1.1 mg per kilogram of body weight of 13-cis-retinoic acid daily.

6. The method of claim 5, wherein said initial period is from about ten days to five months.

7. The method of claim 4, said maintenance dosage is in a range from about 0.14 mg to about 1.1 mg per kilogram of body weight of 13-cisretinoic acid about every three to seven days.

8. The method of claim 4, wherein said composition further comprises a pharmaceutical carrier.

9. The method of claim 8, wherein said composition is in a form selected from the group consisting of powder, pill, capsule, tablet, and liquid.

10. A method of treating palmar and plantar fibromatosis comprising:
   (a) surgically treating an affected area of a patient suffering from palmar or plantar fibromatosis, and
   (b) administering to said patient a therapeutically effective amount of a composition comprising 13-cis-retinoic acid.

11. The method of claim 10, wherein said composition further comprises a pharmaceutical carrier.

12. The method of claim 11, wherein said composition is in a ted from the group consisting of powder, pill, capsule, tablet, and liquid.

* * * * *